(12) United States Patent
Guo et al.

(10) Patent No.: US 12,174,133 B2
(45) Date of Patent: Dec. 24, 2024

(54) X-RAY-BASED TEST DEVICE AND METHOD FOR PLUGGING REMOVAL EFFECT OF SULFUR DISSOLVENT ON SULFUR DEPOSITION ROCK SAMPLE

(71) Applicant: Southwest Petroleum University, Chengdu (CN)

(72) Inventors: Xiao Guo, Chengdu (CN); Pengkun Wang, Chengdu (CN); Tao Li, Chengdu (CN); Jingjing Ma, Chengdu (CN); Changqing Jia, Chengdu (CN); Li Zhou, Chengdu (CN); Ming Zhou, Chengdu (CN); Yi He, Chengdu (CN); Bing Kong, Chengdu (CN); Linkai Li, Chengdu (CN); Lan Wang, Chengdu (CN)

(73) Assignee: Southwest Petroleum University, Chengdu (CN)

( * ) Notice: Subject to any disclaimer, the term of this patent is extended or adjusted under 35 U.S.C. 154(b) by 220 days.

(21) Appl. No.: 18/082,605

(22) Filed: Dec. 16, 2022

(65) Prior Publication Data
US 2023/0194446 A1  Jun. 22, 2023

(30) Foreign Application Priority Data
Dec. 17, 2021  (CN) .......................... 202111554824.X

(51) Int. Cl.
*G01N 23/207*  (2018.01)
(52) U.S. Cl.
CPC ....... *G01N 23/207* (2013.01); *G01N 2223/30* (2013.01); *G01N 2223/601* (2013.01); *G01N 2223/616* (2013.01)

(58) Field of Classification Search
CPC ................ B01D 53/8612; B01D 53/52; B01D 53/1468; G01N 1/00; G01N 2001/002;
(Continued)

(56) References Cited

U.S. PATENT DOCUMENTS

| 2004/0031268 | A1 | 2/2004 | Wilkes et al. |
| 2005/0042376 | A1 | 2/2005 | Xin et al. |
| 2013/0217944 | A1* | 8/2013 | Ayasse .................... B01J 8/001 422/162 |

FOREIGN PATENT DOCUMENTS

| CN | 102053055 A | 5/2011 |
| CN | 108181379 A | 6/2018 |
| CN | 109709021 A | 5/2019 |

* cited by examiner

*Primary Examiner* — Don K Wong
(74) *Attorney, Agent, or Firm* — Bayramoglu Law Offices LLC

(57) ABSTRACT

An X-ray-based test device for a plugging removal effect of a sulfur dissolvent on a sulfur deposition rock sample includes a constant speed and pressure pump, a first intermediate container, a second intermediate container, a first pressure transmitter, a core holder, a second pressure transmitter, a first electric pump, a third intermediate container, a back-pressure valve, a gas flow meter, an $H_2S$ neutralization tank, a second electric pump, a back-pressure transmitter, a confining pressure transmitter, an X-ray generator, an X-ray detector and a thermotank. A sour gas sample is placed in the first intermediate container, and nitrogen is filled in the second intermediate container. The sulfur dissolvent is placed into the third intermediate container. A confining pressure inlet is formed in the core holder. The test device may be used for evaluating the plugging removal effect of the sulfur dissolvent injected into the sulfur deposition rock sample.

13 Claims, 1 Drawing Sheet

(58) Field of Classification Search
CPC ....... G01N 23/20008; G01N 23/20058; G01N 23/20075; G01N 23/207; G01N 2223/01; G01N 2223/03; G01N 2223/05; G01N 2223/056; G01N 2223/60; G01N 2223/616; G01N 2223/601; G01N 2223/307

See application file for complete search history.

X-RAY-BASED TEST DEVICE AND METHOD FOR PLUGGING REMOVAL EFFECT OF SULFUR DISSOLVENT ON SULFUR DEPOSITION ROCK SAMPLE

CROSS REFERENCE TO THE RELATED APPLICATIONS

This application is based upon and claims priority to Chinese Patent Application No. 202111554824.X, filed on Dec. 17, 2021, the entire contents of which are incorporated herein by reference.

TECHNICAL FIELD

The present disclosure relates to the technical field of oil and gas field exploration, in particular to an X-ray-based test device and method for a plugging removal effect of a sulfur dissolvent on a sulfur deposition rock sample.

BACKGROUND

Sour gas reservoirs are widely distributed around the world. The northeast region of Sichuan Basin in China is rich in the sour gas reservoirs, and it is an important part of natural gas production capacity in China. The elemental sulfur dissolved in sour gas will continuously precipitate with a continuous decrease in formation pressure in the exploitation process of the sour gas reservoirs, and meanwhile, the elemental sulfur may also precipitate along with the decomposition of polysulfide, resulting in elemental sulfur deposition to block reservoir pores, cause reservoir damage and reduce the production capacity of sour gas wells.

The serious harm of sulfur deposition in hundreds of wells to gas well production has been reported at home and abroad. In the production of mine fields, the damage to the reservoir permeability by sulfur deposition is usually recovered by injecting a sulfur dissolvent into the formation, so as to improve the reservoir seepage capacity and increase the production capacity of the gas wells. At present, most domestic and foreign researches focus on the experimental evaluation of core damage caused by sulfur deposition. However, there were fewer reports on distribution of the sulfur deposition in the core, as well as test and evaluation of the plugging removal effect of different sulfur dissolvents within the effective swept area.

SUMMARY

In order to solve the above problems, the present disclosure aims to provide an X-ray based test device and method for a plugging removal effect of a sulfur dissolvent on a sulfur deposition rock sample. The change of core density distribution is obtained through X-ray diffraction to a core, and therefore the distribution of sulfur deposition in the core and an effective swept area of the sulfur dissolvent after injection are obtained to comprehensively evaluate the plugging removal effect of the injected sulfur dissolvent.

A technical solution of the present disclosure is as follows:

On the one hand, the present disclosure provides an X-ray based test device for a plugging removal effect of a sulfur dissolvent on a sulfur deposition rock sample, including a constant speed and pressure pump, an intermediate container I, an intermediate container II, a pressure transmitter I, a core holder, a pressure transmitter II, an electric pump I, an intermediate container III, a back-pressure valve, a gas flow meter, an $H_2S$ neutralization tank, an electric pump II, a back-pressure transmitter, a confining pressure transmitter, an X-ray generator, an X-ray detector and a thermotank; a sour gas sample is placed in the intermediate container I, and nitrogen is filled in the intermediate container II, and the sulfur dissolvent is placed into the intermediate container III; a confining pressure inlet is formed in the core holder;

the intermediate container I and the intermediate container II are arranged in parallel, and two ends thereof are connected to an output end of the constant speed and pressure pump and an input end of the core holder respectively; an output end of the core holder is connected to the back-pressure valve by an output pipeline, an output port of the back-pressure valve is connected to the $H_2S$ neutralization tank, and the gas flow meter is arranged on a connected pipeline; the pressure transmitter I and the pressure transmitter II are arranged on two ends of the core holder respectively;

an output end of the electric pump I is connected to an inlet end of the intermediate container III, and an outlet end of the intermediate container III is connected to the output pipeline; an output end of the electric pump II is connected to the back-pressure valve and a confining pressure inlet of the core holder respectively, and the back-pressure transmitter and the confining pressure transmitter are arranged on the connected pipeline respectively;

the X-ray generator and the X-ray detector are symmetrically arranged around a central axis of the core holder, and the X-ray generator is used for emitting X-rays to vertically irradiate the core holder, and the X-ray detector is used for completely receiving the X-rays; and the intermediate container I, the intermediate container II, the core holder and the intermediate container III are all arranged in the thermotank.

Preferably, the test device further includes an emptying valve and a safety valve which are arranged in parallel, and input ends of the emptying valve and the safety valve are connected to a pipeline between the pressure transmitter I and the core holder by a pipeline.

Preferably, the X-ray generator and the X-ray detector are arranged on a mounting base, and the mounting base includes two base brackets; the tops of the two base brackets are connected to circular electric slide rails respectively, and a rectangular sliding bracket formed by fixed straight rods and fixed connecting rods are arranged in the circular electric slide rails; and the X-ray generator and the X-ray detector are oppositely arranged on the two parallel fixed straight rods.

Preferably, the mounting base is arranged in an antiradiation shield.

On the other hand, the present disclosure further provides an X-ray based test method for a plugging removal effect of a sulfur dissolvent on a sulfur deposition rock sample, the X-ray based test device for the plugging removal effect of the sulfur dissolvent on the sulfur deposition rock sample according to any one of claims is used for a test, and the test method includes the following steps:

S1: selecting a target core, and placing it into the core holder after washing and drying, turning on the thermotank and the electric pump II to simulate a formation temperature and pressure;

S2: using the intermediate container II for nitrogen displacement to obtain an initial permeability of the target core;

S3: turning on the X-ray generator and the X-ray detector for conducting X-ray diffraction to the target core to obtain the distribution of a core density;

S4: using the intermediate container I for displacement by a sulfur gas sample to simulate a sulfur deposition process, continuously decreasing a temperature of the thermotank and a pressure of the back-pressure valve in the displacement process, and calculating the permeability and permeability damage rate of the target core in real time;

S5: conducting X-ray diffraction to the target core after sulfur deposition simulation, obtaining the distribution of the core density at the moment, obtaining the distribution of a sulfur deposition amount in the core and the sulfur saturation of the core through calculation, and drawing a distribution map of the sulfur deposition amount at different positions of the core according to the distribution of the sulfur deposition amount in the core;

S6: using the intermediate container III for displacement by the sulfur dissolvent to simulate an injecting process of the sulfur dissolvent, stopping the displacement after an injecting amount of the sulfur dissolvent reaches a target set value, and standing to simulate a soaking process after injection of the sulfur dissolvent; and continuously conducting the X-ray diffraction to the target core in the injecting process and the standing process;

S7: obtaining the change of a mass absorption coefficient from an outlet end of the core to an inlet end of the core according to X-ray diffraction results in step S6, judging a swept position of the sulfur dissolvent according to the mass absorption coefficient, obtaining the distribution of the core density at each moment through calculation, drawing a change curve of an effective swept area of the sulfur dissolvent over time, and performing quantitative analysis on influence of an injection volume and an injection speed of the sulfur dissolvent as well as a soaking time on the effective swept area of the sulfur dissolvent based on the change curve; and meanwhile, obtaining the distribution of a sulfur dissolvent content through calculation, and drawing a distribution map of the sulfur dissolvent content at different positions of the core; and S8: using the intermediate container II for nitrogen displacement, and stopping the displacement after no sulfur dissolvent flows out of the outlet end of the core; and calculating a core permeability and a sulfur dissolving index of the sulfur dissolvent at the moment, evaluating the plugging removal effect of the injected sulfur dissolvent in conjunction with the effective swept area and distribution test results of the sulfur dissolvent.

Preferably, in step S2, the initial permeability of the target core is calculated according to the following formula:

$$K_g = \frac{2ZP_0Q_0\mu L}{Z_0\pi r^2(P_1^2 - P_2^2)} \quad (1)$$

Where: $K_g$ is a test gas permeability of the core in um²; Z is a test gas deviation coefficient under test pressure and temperature, which is a decimal; $P_0$ is atmospheric pressure under standard conditions in atm; $Q_0$ is a test gas flow under the standard conditions in cm³/s; μ is a test gas viscosity under the test temperature and pressure in mPa·s; L is a core length in cm; $Z_0$ is a test gas deviation coefficient under the standard conditions, which is a decimal; r is a core radius in cm; $P_1$ is the pressure at the inlet end of the core in atm; and $P_2$ is the pressure at the outlet end of the core in atm.

Preferably, in step S3, the core density is calculated according to the following formula:

$$\rho_r = \frac{1}{2\lambda_r r}\ln\left(\frac{I}{I_0}\right) \quad (2)$$

Where: $\rho_r$ is a core density of a measuring point in g/cm³; $\lambda_r$ is a mass absorption coefficient of the core, which is dimensionless; r is the core radius in cm; I is an intensity R of rays radiating into the core; and $I_0$ is an initial ray intensity R.

Preferably, in step S5, the target core density after sulfur deposition is calculated according to the following formula:

$$\rho_m = \frac{\frac{1}{2r}\ln\left(\frac{I}{I_0}\right) + \lambda_s\rho_r - \lambda_r\rho_r}{\lambda_s} \quad (3)$$

Where: $\rho_m$ is the density of the core containing deposited sulfur at the measuring point in g/cm³; $\lambda_s$ is a mass absorption coefficient of the deposited sulfur, which is dimensionless; and the sulfur deposition amount in the core is calculated according to the following formula:

$$m_s = \pi r^2(\rho_m - \rho_r)dL \quad (4)$$

Where: $m_s$ is a mass of the deposited sulfur in g; and dL is a diffraction width of a ray measuring point in cm.

Preferably, in step S7, the density of the target core containing the sulfur dissolvent is calculated according to the following formula:

$$\rho_a = \frac{\frac{1}{2r}\ln\left(\frac{I}{I_0}\right) + \lambda_c\rho_m - \lambda_m\rho_m}{\lambda_c} \quad (5)$$

Where: $\rho_a$ is the density of the core containing the sulfur dissolvent at the measuring point in g/cm³; $\lambda_c$ is a mass absorption coefficient of the sulfur dissolvent, which is dimensionless; $\lambda_m$ is the mass absorption coefficient of the core containing the deposited sulfur, which is dimensionless; and the content of the sulfur dissolvent in the core is calculated according to the following formula:

$$m_c = \pi r^2(\rho_a - \rho_m)dL \quad (6)$$

Where: $m_c$ is a mass of the sulfur dissolvent in g.

Preferably, in step S8, the sulfur dissolving index of the sulfur dissolvent is calculated according to the following formula:

$$I_s = \frac{K_1}{K_2} \quad (7)$$

Where: $I_s$ is the sulfur dissolving index of the sulfur dissolvent, which is dimensionless; $K_1$ is the core permeability in um² after the evaluation for a sulfur deposition damage test; $K_2$ is the core permeability after injection of the sulfur dissolvent in um²;

if $I_s<1$, the sulfur dissolvent effectively solves permeability damage caused by core sulfur deposition; if $I_s=1$, the sulfur dissolvent has no obvious effect on core sulfur deposition; and if $I_s>1$, the sulfur dissolvent causes additional pollution to the core; and the smaller the $I_s$, the better the plugging removal effect of the sulfur dissolvent.

The present disclosure has the following beneficial effects:

The present disclosure may quantitatively analyze and evaluate the distribution of the sulfur deposition, as well as the effective swept area and comprehensive effects of the sulfur dissolvent on removal of plugging by deposited sulfur and recovery of the permeability, and it is of great significance in study and evaluation of the plugging removal effect of the sulfur dissolvent injected into the sulfur deposition reservoir of the sour gas well.

BRIEF DESCRIPTION OF THE DRAWINGS

In order to more clearly explain the embodiments of the disclosure or the technical solutions of the prior art, the drawings needed in the description of embodiments or the prior art will be briefly described. Obviously, the drawings in the following description are only some embodiments of the present disclosure. For those ordinarily skilled in the art, other drawings can be obtained in accordance with these drawings without involving any creative work.

In the figure: 1—Constant speed and pressure pump, 2—Thermotank, 3—Intermediate container I, 4—Intermediate container II, 5—Safety valve, 6—Pressure transmitter I, 7—Core holder, 8—Emptying valve, 9—X-ray generator, 10—X-ray detector, 11—Radiation shield, 12—Pressure transmitter II, 13—Electric pump I, 14—Intermediate container III, 15—Confining pressure transmitter, 16—Back-pressure transmitter, 17—H₂S neutralization tank, 18—Gas flow meter, 19—Back-pressure valve, 20—Electric pump II, 21—Fixed straight rod, 22—Fixed connecting rod, 23—Circular electric slide rail and 24—Base bracket.

DETAILED DESCRIPTION OF THE EMBODIMENTS

The present disclosure will be further explained with reference to drawings and embodiments. It should be noted that the embodiments in the present disclosure and technical features in the embodiments may be mutually combined without conflicts. Unless otherwise indicated, all technical and scientific terms used in the present application have the same meaning as commonly understood by those ordinarily skilled in the prior art to which the present application pertains. The words such as "including" or "comprising" publicly used in the present disclosure mean that an element or an object appearing in front of the word covers elements or objects and equivalents listed behind the word, and does not exclude other elements or objects.

Figure 1:
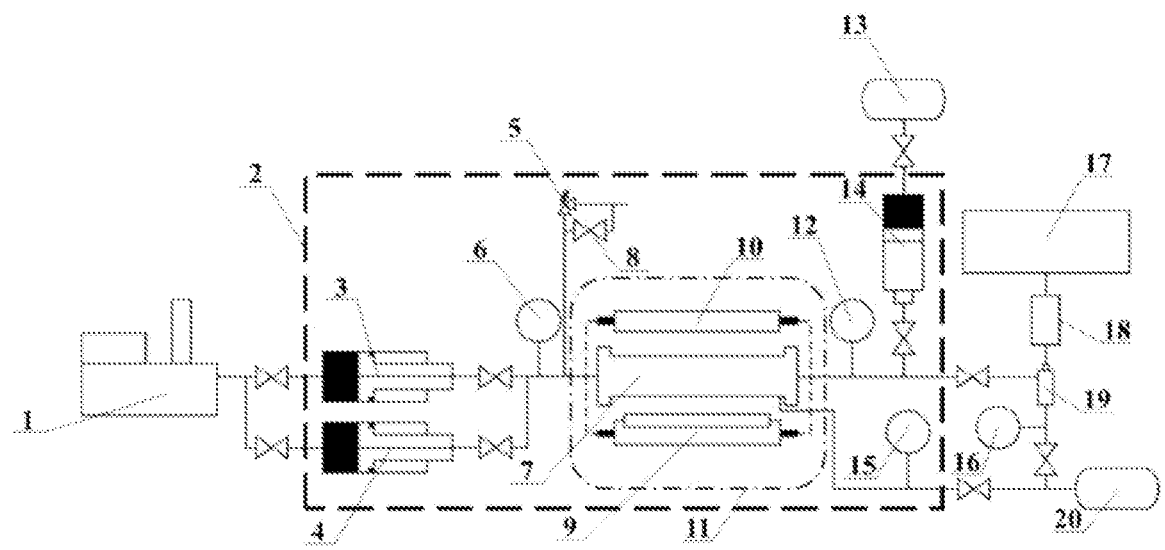
FIG. 1 is a structural schematic diagram of an X-ray-based test device for a plugging removal effect of a sulfur dissolvent on a sulfur deposition rock sample according to the present disclosure.

On the one hand, as shown in FIG. 1, the present disclosure provides an X-ray based test device for a plugging removal effect of a sulfur dissolvent on a sulfur deposition rock sample, including a constant speed and pressure pump 1, an intermediate container I 3, an intermediate container II 4, a pressure transmitter I 6, a core holder 7, a pressure transmitter II 12, an electric pump I 13, an intermediate container III 14, a back-pressure valve 19, a gas flow meter 18, an H₂S neutralization tank 17, an electric pump II 20, a back-pressure transmitter 16, a confining pressure transmitter 15, a ray generator 9, an X-ray detector 10 and a thermotank 2; a sour gas sample is placed in the intermediate container I 3, and nitrogen is filled in the intermediate container II 4, and the sulfur dissolvent is placed into the intermediate container III 14; a confining pressure inlet is formed in the core holder 7;

the intermediate container I 3 and the intermediate container II 4 are arranged in parallel, and two ends thereof are connected to an output end of the constant speed and pressure pump 1 and an input end of the core holder 7 respectively; an output end of the core holder 7 is connected to the back-pressure valve 19 by an output pipeline, an output port of the back-pressure valve 19 is connected to the H₂S neutralization tank 17, and the gas flow meter 18 is arranged on a connected pipeline; the pressure transmitter I 6 and the pressure transmitter II 12 are arranged on two ends of the core holder 7 respectively;

an output end of the electric pump I 13 is connected to an inlet end of the intermediate container III 14, and an outlet end of the intermediate container III 14 is connected to the output pipeline; an output end of the electric pump II 20 is connected to the back-pressure valve 19 and a confining pressure inlet of the core holder 7 respectively, and the back-pressure transmitter 16 and the confining pressure transmitter 15 are arranged on the connected pipeline respectively;

the X-ray generator 9 and the X-ray detector 10 are symmetrically arranged around a central axis of the core holder 7, and the X-ray generator 9 is used for emitting X-rays to vertically irradiate the core holder 7, and the X-ray detector 10 is used for completely receiving the X-rays;

the intermediate container I 3, the intermediate container II 4, the core holder 7 and the intermediate container III 14 are all arranged in the thermotank 2.

The test device in the present disclosure may be used to simulate formation conditions through the thermotank 2, the core holder 7, the back-pressure valve 19, the electric pump II 20 and the like; conduct displacement experiments through the constant speed and pressure pump 1, the intermediate container I 3, the intermediate container II 5, the electric pump I 13, the intermediate container III 14, the H₂S neutralization tank 17 and the like to test the initial permeability of the target core sample and simulate the sulfur deposition and injection of the sulfur dissolvent; conduct the X-ray diffraction to the target core through the X-ray generator 9 and the X-ray detector 10, and obtain the change of the core density distribution according to the X-ray diffraction results so as to obtain the distribution of the sulfur deposition in the core and the effective swept area of the sulfur dissolvent after injection for comprehensively evaluating the plugging removal effect of the injected sulfur dissolvent; and monitor change of data such as pressure and flow in the test process through the pressure transmitter I 6, the pressure transmitter II 12, the gas flow meter 18, the back-pressure transmitter 16, the confining pressure transmitter 15 and the like to provide the basis for calculating the core permeability and other parameters.

In order to improve the safety performance of the present disclosure, the test device further includes an emptying valve 8 and a safety valve 5 which are arranged in parallel, and input ends of the emptying valve 8 and the safety valve 5 are connected to a pipeline between the pressure transmitter I 6 and the core holder 7 by a pipeline.

In one specific embodiment, in order to further improve the safety performance of the present disclosure, an explosion-proof tempered glass cover (not shown in the figure) is arranged at the exterior of the thermotank 2, and a hydrogen sulfide detector and a spraying device (not shown in the figure) are arranged in the explosion-proof tempered glass cover; a sodium hydroxide solution is filled in the spraying device, and both a temperature setting and a fan switch of the thermotank 2 may be remotely controlled by an equipment control system; the spraying device may be remotely turned on by the equipment control system, or automatically starts in case the hydrogen sulfide detector sounds an alarm.

In another specific embodiment, in order to prolong the service life of the present disclosure, all components in contact with a sour gas sample in the test device are made from sulfur-resistant Hastelloy materials, and therefore the resistance to high temperature, high pressure and corrosion thereof is improved; and the maximum pressure for the test device in the present disclosure to withstand on the whole may reach 70 MPa, and the maximum temperature may reach 150° C.

Optionally, in each of the above embodiments, the pressure transmitter I 6, the pressure transmitter II 12, the electric pump I 13, the electric pump II 20, the back-pressure valve 19, the gas flow meter 18, the electric pump II 20, the back-pressure transmitter 16, the confining transmitter 15 and the like are all connected to a computer, and valves on all connecting pipelines are also electrically operated valves; the electrically operated valves are also connected to the computer, and the test device is automatically controlled by a data acquisition panel and an equipment control panel which are built in the computer, as well as data processing software and equipment control software; and therefore, the automation degree of the present disclosure is improved.

In yet another specific embodiment, the core holder 7 is a long core holder for a test experiment of a long core, and in this way, the experiment accuracy may be improved. The long core holder belongs to the prior art, and the specific structure thereof is not described here in detail.

Figure 2:
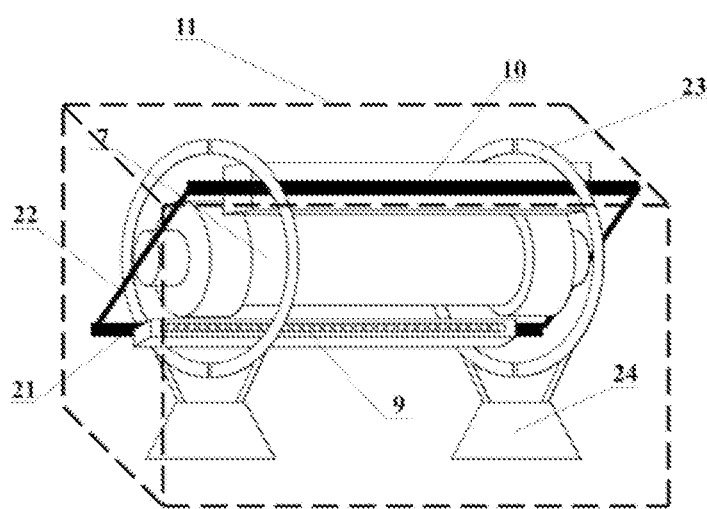
FIG. 2 is a structural schematic diagram of a mounting base of the X-ray-based test device for the plugging removal effect of the sulfur dissolvent on the sulfur deposition rock sample according to the present disclosure.

In yet still another specific embodiment, as shown in FIG. 2, the X-ray generator 9 and the X-ray detector 10 are arranged on a mounting base, the mounting base is arranged in an antiradiation shield 11, and the mounting base includes two base brackets 24; the tops of the two base brackets 24 are connected to circular electric slide rails 23 respectively, and a rectangular sliding bracket formed by fixed straight rods 21 and fixed connecting rods 22 are arranged in the circular electric slide rails 23; and the X-ray generator 9 and the X-ray detector 10 are oppositely arranged on the two parallel fixed straight rods 21. Optionally, the antiradiation shield 11 is a lead shield. In this embodiment, the X-ray generator 9 and the X-ray detector 10 may be symmetrically arranged around a central axis of the core holder 7, and the X-ray generator 9 and the X-ray detector 10 may surround the core holder 7 through rotation of the circular electric slide rails 23 so as to perform comprehensive X-ray diffraction to the core holder 7 and improve the test accuracy.

It should be noted that the circular electric slide rails 23 belong to the prior art, the specific structure thereof is not described here in detail. In addition, except for the mounting method of the X-ray generator 9 and the X-ray detector 10 adopted in the above embodiment, other mounting methods to which rotation by 360° is available in the prior art may also be suitable for the present disclosure.

On the other hand, the present disclosure further provides an X-ray-based test method for a plugging removal effect of a sulfur dissolvent on a sulfur deposition rock sample, and the X-ray-based test device for the plugging removal effect of the sulfur dissolvent on the sulfur deposition rock sample according to any one of claims is used for a test, including the following steps:

S1: a target core is selected, and placed into the core holder 7 after being washed and dried, the thermotank 2 and the electric pump II 20 are turned on to simulate a formation temperature and pressure.

S2: the intermediate container II 4 is used for nitrogen displacement to obtain an initial permeability of the target core; and the initial permeability of the target core is calculated according to the following formula:

$$K_g = \frac{2ZP_0Q_0\mu L}{Z_0\pi r^2(P_1^2 - P_2^2)} \qquad (1)$$

Where: $K_g$ is a test gas permeability of the core in um$^2$; Z is a test gas deviation coefficient under test pressure and temperature, which is a decimal; $P_0$ is atmospheric pressure under standard conditions in atm; $Q_0$ is a test gas flow under the standard conditions in cm$^3$/s; μ is a test gas viscosity under the test temperature and pressure in mPa·s; L is a core length in cm; $Z_0$ is a test gas deviation coefficient under the standard conditions, which is a decimal; r is a core radius in cm; $P_1$ is the pressure at the inlet end of the core in atm; and $P_2$ is the pressure at the outlet end of the core in atm.

S3: the X-ray generator 9 and the X-ray detector 10 are turned on for conducting X-ray diffraction to the target core to obtain the distribution of a core density; the core density is calculated according to the following formula:

$$\rho_r = \frac{1}{2\lambda_r r}\ln\left(\frac{I}{I_0}\right) \qquad (2)$$

Where: $\rho_r$ is a core density of a measuring point in g/cm$^3$; $\lambda_r$ is a mass absorption coefficient of the core, which is dimensionless; r is the core radius in cm; I is an intensity R of rays radiating into the core; and $I_0$ is an initial ray intensity R.

It should be noted that, if X-rays from the X-ray generator may not directly diffract the whole core length, diffraction is conducted on the core from the inlet end to the outlet end in sequence during the X-ray diffraction.

S4: an intermediate container I 3 is used for displacement by the sour gas sample to simulate a sulfur deposition process, a temperature of the thermotank and pressure of the back-pressure valve are continuously reduced in the displacement process, and the permeability and permeability damage rate of the target core are calculated in real time.

In still yet another embodiment, the core permeability at the moment is calculated by a permeability calculation method in step S2, and the permeability damage rate is calculated according to the following formula:

$$PDR_n = \frac{K_i - K_n}{K_i} \times 100\% \qquad (8)$$

Where: $PDR_n$ is the permeability (%) damage rate of the core; $K_i$ is the initial permeability of the core in $um^2$; and $K_n$ is the core permeability after test in $um^2$.

S5: X-ray diffraction is conducted on the target core after sulfur deposition simulation, to obtain the distribution of the core density at the moment, the distribution of a sulfur deposition amount in the core and the sulfur saturation of the core are obtained through calculation, and a distribution map of the sulfur deposition amount at different positions of the core is drawn according to the distribution of the sulfur deposition amount in the core; and the target core density after sulfur deposition is calculated according to the following formula:

$$\rho_m = \frac{\frac{1}{2r}\ln\left(\frac{I}{I_0}\right) + \lambda_s \rho_r - \lambda_r \rho_r}{\lambda_s} \quad (3)$$

Where: $\rho_m$ is the density of the core containing deposited sulfur at the measuring point in $g/cm^3$; $\lambda_s$ is a mass absorption coefficient of the deposited sulfur, which is dimensionless; and the sulfur deposition amount in the core is calculated according to the following formula:

$$m_s = \pi r^2 (\rho_m - \rho_r) dL \quad (4)$$

Where: $m_s$ is a mass of the deposited sulfur in g; and $dL$ is a diffraction width of a ray measuring point in cm.

S6: the intermediate container III 14 is used for displacement by the sulfur dissolvent to simulate an injecting process of the sulfur dissolvent, the displacement is stopped after an injecting amount of the sulfur dissolvent reaches a target set value, and it is left to stand to stimulate a soaking process after the injection of the sulfur dissolvent; the X-ray diffraction is continuously conducted on the target core in the injecting process and the standing process;

S7: the change of a mass absorption coefficient from an outlet end of the core to an inlet end of the core is obtained according to X-ray diffraction results in step S6, a swept position of the sulfur dissolvent is judged according to the mass absorption coefficient (when a mass absorption coefficient at a certain position of the core is not equal to that of the core containing deposited sulfur, it shows that the sulfur dissolvent has swept over this position), the distribution of the core density at each moment is obtained through calculation, a change curve of an effective swept area of the sulfur dissolvent over time is drawn, and quantitative analysis is performed on influence of an injection volume and an injection speed of the sulfur dissolvent as well as a soaking time on the effective swept area of the sulfur dissolvent based on the change curve; meanwhile, the distribution of a sulfur dissolvent content is obtained through calculation, and a distribution map of the sulfur dissolvent content at different positions of the core is drawn; and the density of the target core containing the sulfur dissolvent is calculated according to the following formula:

$$\rho_a = \frac{\frac{1}{2r}\ln\left(\frac{I}{I_0}\right) + \lambda_c \rho_m - \lambda_m \rho_m}{\lambda_c} \quad (5)$$

Where: $\rho_a$ is the density of the core containing the sulfur dissolvent at the measuring point in $g/cm^3$; $\lambda_c$ is a mass absorption coefficient of the sulfur dissolvent, which is dimensionless; $\lambda_m$ is the mass absorption coefficient of the core containing the deposition sulfur, which is dimensionless; and the content of the sulfur dissolvent in the core is calculated according to the following formula:

$$m_c = \pi r^2 (\rho_a - \rho_m) dL \quad (6)$$

Where: $m_c$ is a mass of the sulfur dissolvent in g.

S8: the intermediate container II 4 is used for nitrogen displacement, and the displacement is stopped after no sulfur dissolvent flows out of the outlet end of the core; and a core permeability and a sulfur dissolving index of the sulfur dissolvent at the moment are calculated, the plugging removal effect of the injected sulfur dissolvent is evaluated in conjunction with the effective swept area and distribution test results of the sulfur dissolvent; and the sulfur dissolving index of the sulfur dissolvent is calculated according to the following formula:

$$I_s = \frac{K_1}{K_2} \quad (7)$$

Where: $I_s$ is the sulfur dissolving index of the sulfur dissolvent, which is dimensionless; $K_1$ is the core permeability in $um^2$ after the evaluation for the sulfur deposition damage test; $K_2$ is the core permeability after injection of the sulfur dissolvent in $um^2$;

if $I_s<1$, the sulfur dissolvent effectively relieves permeability damage caused by core sulfur deposition; if $I_s=1$, the sulfur dissolvent has no obvious effect on core sulfur deposition; if $I_s>1$, the sulfur dissolvent causes additional pollution to the core; and the smaller the $I_s$, the better the plugging removal effect of the sulfur dissolvent.

It should be noted that, besides the plugging removal effect of $I_s$, the plugging removal effect of the injected sulfur dissolvent should also need to be comprehensively evaluated according to the effect swept area and distribution test results of the sulfur dissolvent. The larger the effective swept area, the better the plugging removal effect of the sulfur dissolvent, the more uniform the distribution, and the better the effect.

In a specific test experiment for the plugging removal effect of the sulfur dissolvent injected into a sulfur deposition rock sample, the sulfur dissolvent for test is an efficient sulfur dissolvent, and the efficient sulfur dissolvent includes 80% of dimethyl disulfide (DMDS) and 20% of dimethylacetamide (DMA). The temperature, pressure, displacement speed, an injection volume of the sulfur dissolvent, a sulfur dissolvent speed, a standing time of the sulfur dissolvent after injection and other parameters in the test experiment may be designed according to a similarity principle, and are compared with those practically used on site, so that the experimental results are applied to the actual production on site to improve the practical performance.

It should be noted that, after completion of step S8, the test method further includes step S9 that the emptying valve is turned on to empty gas in the pipeline into the $H_2S$ neutralization tank for treating the gas sample, and the whole test device is repeatedly washed with nitrogen to prevent each component of the test device from being corroded by the sour gas sample.

The above descriptions are only the preferred embodiments of the disclosure, which are not intended to limit the present disclosure in any form; the preferred embodiments of the present disclosure have been disclosed as above-mentioned, which are not intended to limit the present disclosure; minor alteration or modification as an equivalent embodiment of an equivalent change may be made by any person skilled in the prior art according to the technical contents disclosed above without departing from the scope of the technical solutions of the present disclosure; and any simple amendment, equivalent change and modification made to the above embodiments according to the technical essence of the present disclosure, without deviating from the technical solutions of the present disclosure, still fall within the scope of the technical solutions of the present disclosure.

What is claimed is:

1. An X-ray-based test device for a plugging removal effect of a sulfur dissolvent on a sulfur deposition rock sample, comprising a constant speed and pressure pump, a first intermediate container, a second intermediate container, a first pressure transmitter, a core holder, a second pressure transmitter, a first electric pump, a third intermediate container, a back-pressure valve, a gas flow meter, an $H_2S$ neutralization tank, a second electric pump, a back-pressure transmitter, a confining pressure transmitter, an X-ray generator, an X-ray detector and a thermotank; wherein a sour gas sample is placed in the first intermediate container, nitrogen is filled in the second intermediate container, and the sulfur dissolvent is placed into the third intermediate container; a confining pressure inlet is formed in the core holder;

the first intermediate container and the second intermediate container are arranged in parallel, and two ends of the first intermediate container are connected to an output end of the constant speed and pressure pump and an input end of the core holder respectively; an output end of the core holder is connected to the back-pressure valve by an output pipeline, an output port of the back-pressure valve is connected to the $H_2S$ neutralization tank, and the gas flow meter is arranged on a connected pipeline; the first pressure transmitter and the second pressure transmitter are arranged on two ends of the core holder respectively;

an output end of the first electric pump is connected to an inlet end of the intermediate third container, and an outlet end of the third intermediate container is connected to the output pipeline; an output end of the second electric pump is connected to the back-pressure valve and the confining pressure inlet of the core holder respectively, and the back-pressure transmitter and the confining pressure transmitter are arranged on the connected pipeline respectively;

the X-ray generator and the X-ray detector are symmetrically arranged around a central axis of the core holder, wherein the X-ray generator is configured to emit X-rays to vertically irradiate the core holder, and the X-ray detector is configured to completely receive the X-rays; and the first intermediate container, the second intermediate container, the core holder and the third intermediate container are arranged in the thermotank.

2. The X-ray-based test device according to claim 1, further comprising an emptying valve and a safety valve, wherein the emptying valve and the safety valve are arranged in parallel, and an input end of the emptying valve and an input end of the safety valve are connected to a first pipeline between the first pressure transmitter and the core holder by a second pipeline.

3. The X-ray-based test device according to claim 1, wherein the X-ray generator and the X-ray detector are arranged on a mounting base, and the mounting base comprises two base brackets; tops of the two base brackets are connected to circular electric slide rails respectively, and a rectangular sliding bracket formed by fixed straight rods and fixed connecting rods is arranged in the circular electric slide rails; and the X-ray generator and the X-ray detector are oppositely arranged on the fixed straight rods parallel to each other.

4. The X-ray-based test device according to claim 3, wherein the mounting base is arranged in an anti-radiation shield.

5. An X-ray-based test method for a plugging removal effect of a sulfur dissolvent on a sulfur deposition rock sample, wherein the X-ray-based test device according to claim 1 is configured for a test, and the X-ray-based test method comprises:

S1: selecting a target core, and placing the target core into the core holder after washing and drying, turning on the thermotank and the second electric pump to simulate a formation temperature and pressure;

S2: using the second intermediate container for nitrogen displacement to obtain an initial permeability of the target core;

S3: turning on the X-ray generator and the X-ray detector for conducting X-ray diffraction to the target core to obtain a distribution of a core density;

S4: using the first intermediate container for displacement by the sour gas sample to simulate a sulfur deposition process, continuously decreasing a temperature of the thermotank and a pressure of the back-pressure valve in a displacement process, and calculating a permeability and a permeability damage rate of the target core in real time;

S5: conducting X-ray diffraction to the target core after sulfur deposition simulation, obtaining the distribution of the core density at the moment, obtaining a distribution of a sulfur deposition amount in the target core and a sulfur saturation of the target core through calculation, and drawing a distribution map of the sulfur deposition amount at different positions of the target core according to the distribution of the sulfur deposition amount in the target core;

S6: using the third intermediate container for displacement by the sulfur dissolvent to simulate an injecting process of the sulfur dissolvent, stopping the displacement after an injecting amount of the sulfur dissolvent reaches a target set value, and standing to simulate a soaking process after injection of the sulfur dissolvent; and continuously conducting the X-ray diffraction to the target core in the injecting process and a standing process;

S7: obtaining a change of a mass absorption coefficient from an outlet end of the target core to an inlet end of the target core according to X-ray diffraction results in step S6, judging a swept position of the sulfur dissolvent according to the mass absorption coefficient, obtaining the distribution of the core density at each moment through calculation, drawing a change curve of an effective swept area of the sulfur dissolvent over time, and performing quantitative analysis on influence of an injection volume and an injection speed of the sulfur dissolvent and a soaking time on the effective swept area of the sulfur dissolvent based on the change curve; and meanwhile, obtaining a distribution of a sulfur dissolvent content through calculation, and drawing a distribution map of the sulfur dissolvent content at different positions of the target core; and S8: using the second intermediate container for nitrogen displacement, and stopping the displacement after no sulfur dissolvent flows out of the outlet end of the target core; and calculating a core permeability and a sulfur dissolving index of the sulfur dissolvent at the moment, evaluating a plugging removal effect of the injected sulfur dissolvent in conjunction with the effective swept area and distribution test results of the sulfur dissolvent.

6. The X-ray-based test method according to claim 5, wherein in step S2, the initial permeability of the target core is calculated according to the following formula:

$$K_g = \frac{2ZP_0Q_0\mu L}{Z_0\pi r^2(P_1^2 - P_2^2)} \tag{1}$$

wherein $K_g$ is a test gas permeability of the target core in $um^2$; Z is a test gas deviation coefficient under test pressure and temperature, and Z is a decimal; $P_0$ is atmospheric pressure under standard conditions in atm; $Q_0$ is a test gas flow under standard conditions in $cm^3/s$; $\mu$ is a test gas viscosity under the test pressure and temperature in mPa·s; L is a core length in cm; $Z_0$ is a test gas deviation coefficient under the standard conditions, and $Z_0$ is a decimal; r is a core radius in cm; $P_1$ is a pressure at the inlet end of the target core in atm; and $P_2$ is a pressure at the outlet end of the target core in atm.

7. The X-ray based test method according to claim 5, wherein in step S3, the core density is calculated according to the following formula:

$$\rho_r = \frac{1}{2\lambda_r r}\ln\left(\frac{I}{I_0}\right) \tag{2}$$

wherein $\rho_r$ is a core density of a measuring point in $g/cm^3$; $\lambda_r$ is the mass absorption coefficient of the target core, and $\lambda_r$ is dimensionless; r is a core radius in cm; I is an intensity R of rays radiating into the target core; and $I_0$ is an initial ray intensity R.

8. The X-ray based test method according to claim 7, wherein in step S5, the density of the target core after sulfur deposition is calculated according to the following formula:

$$\rho_m = \frac{\frac{1}{2\lambda_r r}\ln\left(\frac{I}{I_0}\right) + \lambda_s\rho_r - \lambda_r\rho_r}{\lambda_s} \tag{3}$$

wherein $\rho_m$ is the density of the target core containing deposited sulfur at the measuring point in $g/cm^3$; $\lambda_s$ is a mass absorption coefficient of the deposited sulfur, and $\lambda_s$ is dimensionless; and the sulfur deposition amount in the target core is calculated according to the following formula:

$$m_s = \pi r^2(\rho_m - \rho_r)dL \tag{4}$$

wherein $m_s$ is a mass of the deposited sulfur in g; and dL is a diffraction width of a ray measuring point in cm.

9. The X-ray based test method according to claim 8, wherein in step S7, the density of the target core containing the sulfur dissolvent is calculated according to the following formula:

$$\rho_a = \frac{\frac{1}{2r}\ln\left(\frac{I}{I_0}\right) + \lambda_c\rho_m - \lambda_m\rho_m}{\lambda_c} \tag{5}$$

wherein $\rho_a$ is the density of the target core containing the sulfur dissolvent at the measuring point in $g/cm^3$; $\lambda_c$ is the mass absorption coefficient of the sulfur dissolvent, and $\lambda_c$ is dimensionless; $\lambda_m$ is the mass absorption coefficient of the target core containing the deposited sulfur, and $\lambda_m$ is dimensionless; and the sulfur dissolvent content in the target core is calculated according to the following formula:

$$m_c = \pi r^2(\rho_a - \rho_m)dL \tag{6}$$

wherein $m_c$ is a mass of the sulfur dissolvent in g.

10. The X-ray based test method according to claim 5, wherein in step S8, the sulfur dissolving index of the sulfur dissolvent is calculated according to the following formula:

$$I_s = \frac{K_1}{K_2} \tag{7}$$

wherein $I_s$ is the sulfur dissolving index of the sulfur dissolvent, and $I_s$ is dimensionless; $K_1$ is the core permeability in $um^2$ after an evaluation for a sulfur deposition damage test; $K_2$ is the core permeability after injection of the sulfur dissolvent in $um^2$;

wherein when $I_s<1$, the sulfur dissolvent effectively solves permeability damage caused by core sulfur deposition; when $I_s=1$, the sulfur dissolvent has no obvious effect on the core sulfur deposition; when $I_s>1$, the sulfur dissolvent causes additional pollution to the target core; and the plugging removal effect of the sulfur dissolvent increases as $I_s$ decreases.

11. The X-ray-based test method according to claim 5, wherein the X-ray-based test device further comprises an emptying valve and a safety valve, wherein the emptying valve and the safety valve are arranged in parallel, and an input end of the emptying valve and an input end of the safety valve are connected to a first pipeline between the first pressure transmitter and the core holder by a second pipeline.

12. The X-ray-based test method according to claim 5, wherein the X-ray generator and the X-ray detector are arranged on a mounting base, and the mounting base comprises two base brackets; tops of the two base brackets are connected to circular electric slide rails respectively, and a rectangular sliding bracket formed by fixed straight rods and fixed connecting rods is arranged in the circular electric slide rails; and the X-ray generator and the X-ray detector are oppositely arranged on the fixed straight rods parallel to each other.

13. The X-ray-based test method according to claim 12, wherein the mounting base is arranged in an anti-radiation shield.

* * * * *